United States Patent [19]

Aldrovandi et al.

[11] Patent Number: 4,668,945
[45] Date of Patent: May 26, 1987

[54] DETECTOR OF BUBBLES IN BLOOD

[75] Inventors: Mauro Aldrovandi; Mauro Facchini, both of Mirandola, Italy

[73] Assignee: Hospal A.G., Meyzieu, France

[21] Appl. No.: 791,493

[22] Filed: Oct. 25, 1985

[30] Foreign Application Priority Data

Oct. 31, 1984 [IT] Italy ............... 53987/84[U]

[51] Int. Cl.⁴ ............................................. G08B 21/00
[52] U.S. Cl. ................... 340/621; 73/290 V; 128/660; 310/335; 310/339; 367/908
[58] Field of Search ............... 340/621, 606, 608, 609; 73/19, 61 R, 290 V, 622; 436/68; 310/335, 339; 128/660, DIG. 13; 367/908, 188

[56] References Cited

U.S. PATENT DOCUMENTS 3,411,344 11/1968 Lloyd ................... 73/622 X
3,921,622 11/1975 Cole ................... 73/61 R X
3,935,876 2/1976 Massie et al. ........... 128/DIG. 13 X
3,974,681 8/1976 Namery ................ 128/DIG. 13 X
4,114,144 9/1978 Hyman ................ 128/DIG. 13 X
4,418,565 12/1983 St. John ................... 73/19
4,432,231 2/1984 Napp et al. ........... 73/290 V Primary Examiner—James L. Rowland
Assistant Examiner—Daniel Myer
Attorney, Agent, or Firm—Gerald D. Sharkin; Robert S. Honor; Walter F. Jewell

[57] ABSTRACT

A device for detecting the presence of a gaseous fluid in relation to a predetermined level of liquid in an elastically deformable vessel comprises a U-shaped body capable of accommodating within it a portion of the vessel at a predetermined liquid level. A pair of piezoelectric transducers in the body, used as transmitter and receiver, is fixed face-to-face on opposite arms of the U-shaped body. The device moreover comprises a cover capable of confining the portion of the vessel inside the U-shaped body, and an elastic device disposed between the cover and the U-shaped body and capable of producing an elastic deformation of the vessel and causing the contact surfaces of transducers to contact intimately the said portion of the vessel without entrapment of air.

19 Claims, 4 Drawing Figures

DETECTOR OF BUBBLES IN BLOOD

FIELD OF THE INVENTION

The present invention concerns a device detecting the presence of a gaseous fluid in relation to a predetermined level of a liquid in a vessel. More particularly, this invention concerns a device using, as a means for detecting the presence of a gaseous fluid, transducers capable of transmitting and of receiving a signal which is sensitive to the presence of a gaseous fluid. For this purpose, it is preferable to use piezoelectric transducers capable of transmitting and of receiving ultrasonic frequency signals whose propagation is strongly affected by the presence of a gaseous fluid even in very small quantities.

PRIOR ART

To prevent air from being trapped between the transducers and the corresponding facing surfaces of the vessel in which the measurement is to be effected, it is known to use elastic means which push the transducers against the respective facing surfaces of the vessel. These means are generally helical springs accommodated within a body supporting the vessel and elastically pushing the support elements of the transducers along slides arranged in the body of the apparatus. In one variant of such an embodiment, one of the transducers is fixed to the body of the apparatus, while the other is detachable and is connected to the body of the apparatus by a helical spring.

Whilst the known devices mentioned above effectively make it possible to detect the presence of a gaseous fluid with reasonable accuracy and reliability, they are particularly expensive, essentially because of the cost of manufacturing very accurate guides for the supporting elements for the transducers.

Moreover, the use of a detector device wherein it is only one of the transducers that is detachable, renders the preparatory operation for the measurement more complex because it is necessary to maintain the spring stretched with one hand and to position the vessel correctly between the two transducers with the other hand.

OBJECT OF THE INVENTION

It is an object of the present invention to provide a detector device which would allow the drawbacks of the known devices mentioned above to be overcome, and in particular to provide a device which does not require the execution of accurate guides for the support of the transducers and which should, moreover, be easy to use.

SUMMARY OF THE INVENTION

This object is attained by the present invention which provides a device for detecting the presence of a gaseous fluid in relation to a predetermined level of liquid in a deformable and elastic vessel, such device comprising:

a hollow body having a compartment capable of accommodating a portion of the said vessel disposed in relation to said predetermined level;

a pair of transducers, respectively transmitting and receiving a predetermined signal, said transducers being fixed to said hollow body in diametrically opposite positions and facing each other and said compartment, the receiver transducer being capable of cooperating with the said transmitter transducer and of emitting a signal responsive to the quantity of gaseous fluid interposed between said transducers; and a movable element connected to said hollow body by elastic means and capable of transmitting a radial thrust which can create a deformation of said portion of the vessel and its intimate contact with the transducers in opposite zones without air entrapment therebetween.

BRIEF DESCRIPTION OF THE DRAWINGS

To render the present invention more readily understood, there will now be described a preferred embodiment by way of a non-restrictive example and with reference to the accompanying drawings wherein.

DESCRIPTION OF THE PREFERRED EMBODIMENT

Figure 1:
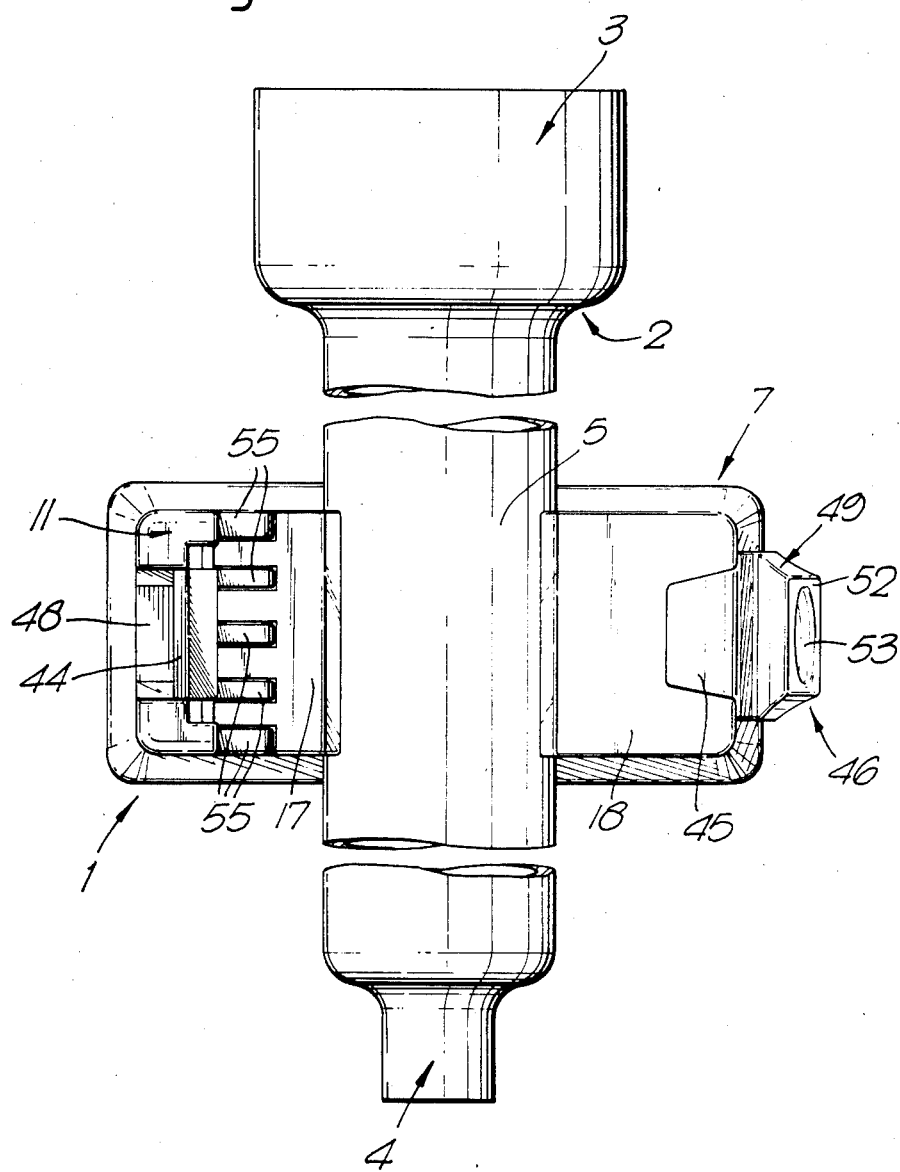
FIG. 1 is an elevational view of a detector device disposed around a vessel and illustrated in the open condition with a tubular vessel therein ready for a measurement.
Figure 2:
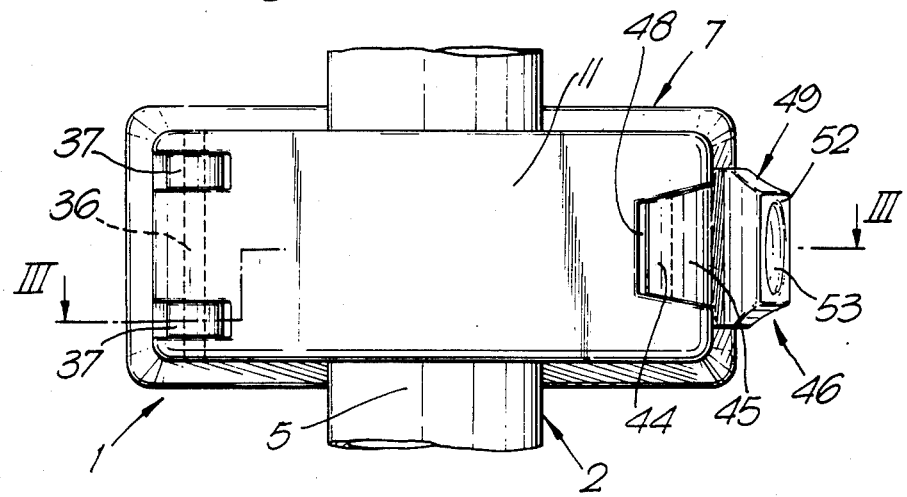
FIG. 2 shows the device of FIG. 1 in the closed condition ready for detecting a gaseous fluid within the said vessel.

Referring to FIGS. 1 and 2 in particular, there can be seen a device 1 for detecting the presence of a gaseous fluid in relation to a predetermined level of liquid in a vessel 2. Vessel 2 is essentially of a tubular type with walls which are partially elastically deformable. The tubular vessel 2 has an upper opening 3 enlarged for the entry of a liquid and a convergent lower opening 4 for the emergence of the same liquid. Advantageously, the vessel 2 could be incorporated along an extracorporeal blood circuit in which case blood would be the liquid within which one would wish to detect the presence of gaseous fluid. The device 1 is capable of accommodating a portion 5 of the vessel 2 between the upper opening 3 and the lower opening 4 of the vessel 2 itself.

Figure 3:
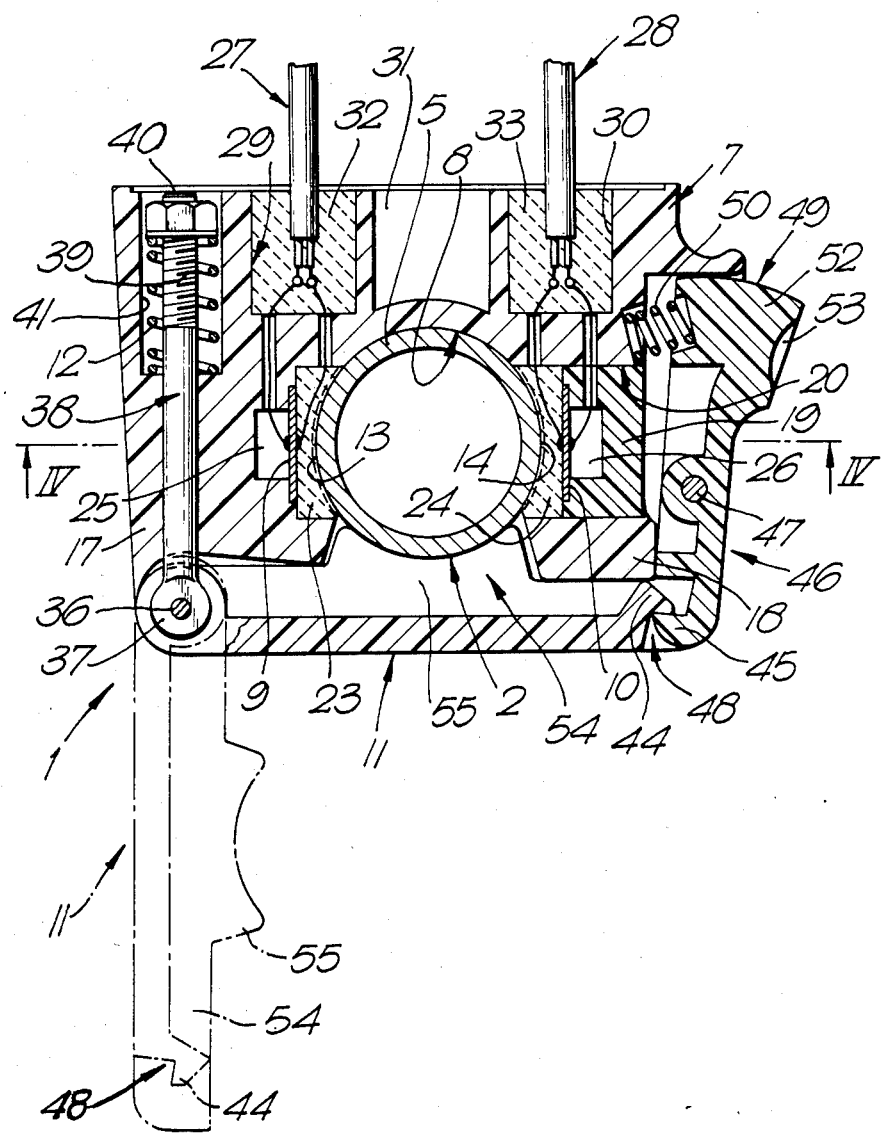
FIG. 3 is a cross-sectional view taken along the plane III,III of FIG. 2.

Referring more particularly to FIG. 3, the device 1 essentially comprises:

a hollow body 7 having a compartment 8 capable of accommodating the intermediate portion 5 of vessel 2;

a pair of transducers 9, 10 (FIGS. 3 and 4) of the piezoelectric type, used respectively as transmitter and receiver of an ultrasonic frequency signal, the transducers being fixed to the body 7 in diametrically opposite positions and facing each other relative to the intermediate portion 5 of the vessel, and facing the compartment 8; and a cover 11 connected to the body 7 by a helical compression spring 12 (FIG. 3) as will be described in greater detail below, the essential function being to transmit a radial thrust to the portion 5 of vessel 2 with the purpose of entailing a deformation, and as a result, the intimate contact of the opposite sides 13, 14 of intermediate portion 5 with the transducers 9 and 10 without trapping any air between the contacting surfaces.

Examining the device 1 in greater detail, it will be observed that the hollow body 7 is essentially U-shaped and that it supports transducers 9 and 10 by means of respective limbs 17 and 18. In particular, the transducer 9 is supported directly by limb 17, whilst the other transducer 10 is supported by an element 19 force-fitted within a transverse hole 20 in the other limb 18.

Figure 4:
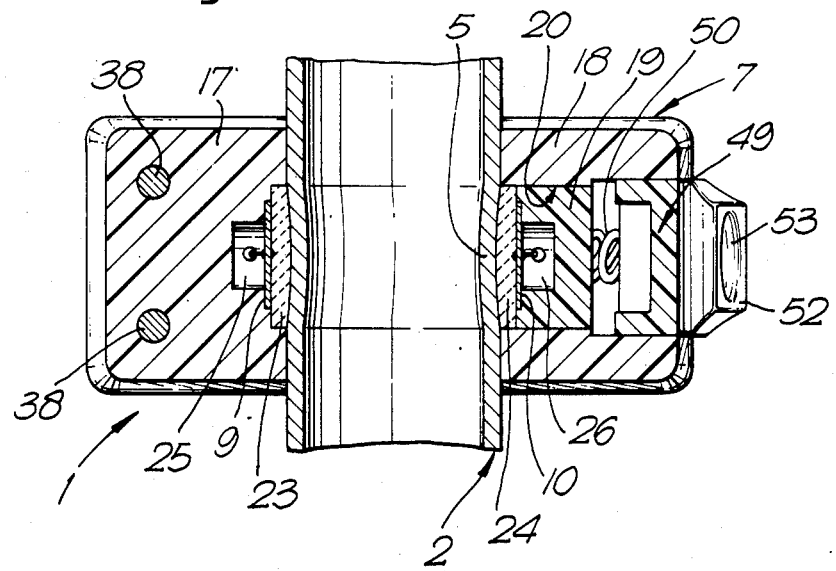
FIG. 4 is a cross-sectional view taken along the plane IV—IV of FIG. 3.

The compartment 8 is constructed in such a way as to be slightly elliptical, the major axis of the ellipse being identical with the common axis of symmetry of the two transducers 9 and 10. On their faces turned towards the compartment 8, these transducers are covered by a layer 23, 24 of a plastic material, such as an epoxy resin. Referring to FIGS. 3 and 4, it will be observed that the free surface of each layer 23, 24 has the shape of a saddle so as to create a slight restriction of the portion of the compartment 8 in contact with the intermediate vessel portion 5 in which the presence of the gaseous fluid is to be detected.

On the side of each transducer remote from the compartment 8 are two chambers 25, 26 which allow the piezoelectric transmitter transducer 9 and the receiver transducer 10 to vibrate. The facing sides of each transducer 9, 10 are connected by fine conducting wires to electric conductors 27, 28; in particular, the connection between the fine conducting wires and the conductors 27 and 28 is effected inside the respective chambers 29 and 30 in the intermediate bight portion 31 of the U-shaped body 7 and they are advantageously filled with a setting resin 32, 33 of a suitable plastic material.

Referring to FIGS. 2, 3 and 4, it will be observed that the cover 11 has an essentially rectangular shape and that it can pivot around a pin 36 (FIGS. 2 and 3) supported by the ends 37 of a pair of rods 38 each of which can slide inside a longitudinal housing within the limb 17. Each rod 38 has, on its end remote from the pin 36, a threaded portion 39 (see FIG. 3) on which a nut 40 is screwed. The housing for each rod 38 is essentially enlarged in the vicinity of the threaded portion 39 to constitute a cylindrical chamber 41 which contains the above-mentioned helical spring 12, which is coaxial with the rod 38 and can be pre-strained by the tightening of the nut 40.

On the opposite side of the cover 11 to that which turns around the pin 36, is a catch 44 capable of cooperating with a corresponding catch 45 disposed at the end of an arm 46 capable of pivoting around a pin 47 fixed transversely to the limb 18 of the body 7. Referring to FIG. 2, it will be seen that the catch 45 of the pivoting arm 46 is essentially trapezoidal in shape and narrows towards the end, whilst the catch 44 is situated below a recess 48, also of a trapezoidal shape and complementary to that of the catch 45 so as to facilitate the locking of the catch 45 on catch 44.

On the end remote from that comprising the catch 45 the pivoting arm 46 has an end 49 which delimits a part of the housing for a helical compression spring 50. Such a spring is comprised between the said end 49 of the pivoting arm 46 and the adjacent outwardly facing surface of the limb 18 of the body 7 and transmits to the pivoting arm 46 a resilient thrust capable of causing the arm 46 to turn in a clockwise direction (see FIG. 3) so as to facilitate the fastening of the catch 44 of the cover 11 with the catch 45 of the pivoting arm 46.

On its opposite side facing away from the spring 50, the end 49 of the arm 46 has a bulge 52 essentially forming a pyramid frustum on whose surface is a circular hollow concave area 53.

Finally it will be observed, by referring to FIGS. 1 and 3, that the cover 11 has, on its side facing the compartment 8 of the hollow body 7, a plurality of longitudinal parallel ribs 54 which each extend essentially from the pivot end near pin 36 as far as the opposite end provided with the catch 44. In the portion facing the compartment 8 each rib 54 has a profile which essentially constitutes the arc of an ellipse to complete and close the compartment 8.

The device 1 is used as follows:

First of all, the vessel 2 is inserted in the compartment 8, as shown in FIG. 1. Then the cover 11 is closed by swinging it across and pushing it until the catch 45 is locked on the catch 44 (see FIG. 2). In these conditions, the cover 11 is maintained against the hollow body 7 on the one side by the catch 44 and on the opposite side by the pin 36 and rods 38.

Since the rods 38 are subjected to axial elastic traction under the effect of the coil springs 12, it follows that the cover 11 transmits to the intermediate part 5 of the vessel 2, a radial compressive force through the intermediary of the elliptical profiles 55 of the longitudinal ribs 54. Such radial forces result in the deformation of the vessel portion 5 comprising the opposite zones 13, 14 so as to cause them to press intimately, without trapping any air, against the opposite surfaces 23, 24 of the transducers 9 and 10. The deformation of the intermediate portion 5 of the vessel 2 in the direction of the transducers 9 and 10 is promoted by the fact that the compartment 8 is partially elliptical and, as already mentioned, has its major axis aligned in the direction of vibration of the transducers.

In these conditions, the device 1 is ready to be used as a detector for the presence of a gaseous fluid at the level of the intermediate portion 5 of the vessel 2. For this purpose, it suffices to provide the transmitter transducer 9 with a predetermined frequency signal, an ultrasonic one for example, and to pick up the corresponding electric signal from the receiver transducer 10. Since, as is known, the amplitude of the electric signal delivered by the receiver transducer 10 depends on the presence of a gaseous fluid, for instance, very fine air bubbles, between the transducers 9 and 10, it will be sufficient to compare the effective value of such an amplitude with a reference value in order to detect the possible presence of a gaseous fluid at the level of the intermediate zone 5.

It is obvious that the device 1 can equally well be used for detecting the presence of a gaseous fluid in the liquid of the vessel 2, as for detecting the lowering of the level of such a liquid below the zone between, and under the control of, the transducers 9 and 10.

When it is desired to withdraw vessel 2, it suffices to press with one finger on the hollow circular area 53 at the end 49 of the pivoting arm 46 (FIG. 3) to effect rotation of the pivoting arm 46 in an anticlockwise direction around pin 47 and to compress the spring 50 until the catch 45 releases the catch 44 of the cover 11. The cover then swings open by partially rotating around pin 36 under the effect of the elastic reaction exerted by the intermediate portion 5 of vessel 2, and it can then be opened completely by the operator to the position indicated in dashed lines in FIG. 3.

An examination of the characteristics of the detector device in accordance with the present invention makes it possible to reveal the advantages obtained. In particular, the making of accurate guides for the supporting elements of the piezoelectric transducers is unnecessary, since the transducers are fixed on the hollow body 7. The body 7 can be injection moulded which contributes to a reduction in the cost of device 1. Moreover, the operations needed for arranging the vessel 2 in the compartment 8 and then for closing cover 11 are elementary and can be easily performed with one hand.

Finally, it is clear that various modifications and variants of the embodiment can be applied by the expert to device 1 described above without thereby departing from the scope of the present invention.

We claim:

1. In a device for detecting the presence of a gaseous fluid in relation to a predetermined level of liquid in a portion of a deformable and elastic vessel; the improvement comprising:
   (a) a hollow body defining a compartment capable of accommodating said portion of said vessel disposed in relation to said predetermined level;
   (b) transmitter transducer means for emitting a predetermined signal;
   (c) receiver transducer means for receiving said predetermined signal emitted by the transmitter means, said transmitter and receiver transducer means being fixed to said hollow body in diametrically opposite positions facing each other, and facing said compartment; said receiver transducer means being capable of cooperating with the said transmitter transducer and of emitting an output signal responsive to the quantity of the gaseous fluid interposed between said transducer means;
   (d) movable means to said hollow body and adapted to bear against said portion of the vessel; and
   (e) resilient biasing means connecting said movable means to said hollow body and capable of biasing said movable means to transmit a radial thrust against said portion of the vessel to create a deformation of the vessel portion and intimate contact between it and the transmitter and receiver transducer means without air entrapment therebetween.

2. A device according to claim 1, wherein said hollow body is essentially U-shaped having opposite limbs carrying said transmitter transducer means and receiver transducer means, respectively, said movable means being capable of confining said vessel inside said hollow body.

3. A device according to claim 2, wherein said movable means comprise a cover swingable around a pivot pin at the end of a first said limb of said hollow body, and wherein fastener means are provided for fastening said cover at the end of the second said limb.

4. A device according to claim 3, including means slidably supporting said pin on said first limb, said supporting means including rod means axially movable against the action of said resilient biasing means.

5. A device according to claim 4, wherein said resilient biasing means comprise at least one helical spring coaxial with said rod means and capable of exerting an elastic thrust on said pin tending to bring said pin and said cover towards the distal ends of said first and second limbs of said U-shaped body.

6. A device according to claim 5, including means defining a cylindrical chamber at the base of the said first limb, said spring being accommodated within said cylindrical chamber.

7. A device according to claim 3, wherein said fastener means comprise a pivoting arm, first catch means provided at one end of said arm, and second catch means on the end of said cover and capable of engaging said first catch means.

8. A device according to claim 7, wherein said first catch means on said pivoting arm is tapering and said second catch means comprises means defining a tapered recess near the end of said cover, said tapering first catch means being capable of engagement in said recess.

9. A device according to claim 8, wherein said first catch means and said recess are substantially trapezoidal in shape.

10. A device according to claim 7, including a pin carried by said second limb of the said U-shaped hollow body, and wherein said arm pivots around said pin.

11. A device according to claim 10, including elastic means biasing said arm for pivoting around said pin in a first direction.

12. A device according to claim 11, wherein said elastic means are interposed between firstly an end of the pivoting arm which is on the side thereof opposite to the first catch means and secondly the facing surface of the said second limb of the hollow body.

13. A device according to claim 12, including an outwardly extending boss on said end of the pivoting arm; and dish means delimiting an actuating zone for the rotation of the pivoting arm.

14. A device according to claim 2, wherein the hollow body includes chambers which allow said transducer means to vibrate and wherein each of said transducer means is of the piezoelectric type and, on the side opposite to that which faces towards the compartment, the transducer means faces a said chamber and wherein one said chamber is arranged inside the said first limb of said U-shaped body, and the other said chamber is arranged in a transducer-supporting element carrying its associated said transducer, said supporting element being fixed to said second limb of said U-shaped body.

15. A device according to claim 14, wherein said second limb of the U-shaped hollow body includes means defining a hole, and wherein said transducer-supporting element is force-fitted in said hole.

16. A device according to claim 1, wherein each of said transmitter transducer means and receiver transducer means has a surface directed towards said compartment and covered with a layer of a protective material.

17. A device according to claim 16, wherein said material is an epoxy resin.

18. A device according to claim 1, wherein the hollow body includes chambers which allow said transducer means to vibrate and wherein each of said transducer means is of the piezoelectric type and, on the side opposite to that which faces towards the compartment, the transducer means faces a said chamber.

19. A device according to claim 1, wherein said compartment has an elliptical cross-section whose major axis coincides with the axis of symmetry common to the said transmitter transducer means and said receiver transducer means.

* * * * *